(12) United States Patent
Umekawa et al.

(10) Patent No.: US 9,636,014 B2
(45) Date of Patent: May 2, 2017

(54) OPHTHALMOLOGIC APPARATUS AND ALIGNMENT METHOD

(71) Applicant: CANON KABUSHIKI KAISHA, Tokyo (JP)

(72) Inventors: Kazuaki Umekawa, Machida (JP); Hiroshi Itoh, Yokohama (JP); Wataru Sakagawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/949,820

(22) Filed: Jul. 24, 2013

(65) Prior Publication Data

US 2014/0028977 A1 Jan. 30, 2014

(30) Foreign Application Priority Data

Jul. 30, 2012 (JP) ................................ 2012-167919

(51) Int. Cl.
*A61B 3/103* (2006.01)
*A61B 3/14* (2006.01)
*A61B 3/15* (2006.01)

(52) U.S. Cl.
CPC .............. *A61B 3/152* (2013.01); *A61B 3/103* (2013.01); *A61B 3/14* (2013.01)

(58) Field of Classification Search
CPC ......... A61B 3/14; A61B 3/102; A61B 3/0025; A61B 3/12; A61B 3/113; A61B 3/0008;
(Continued)

(56) References Cited

U.S. PATENT DOCUMENTS 5,120,123 A * 6/1992 Akiyama ............. A61B 3/1225
351/205
5,537,163 A 7/1996 Ueno
(Continued)

FOREIGN PATENT DOCUMENTS

CN 1471893 A 2/2004
CN 1868397 A 11/2006
(Continued)

OTHER PUBLICATIONS

Chinese Office Action issued in corresponding application 201310325640.5 dated Dec. 15, 2014.
(Continued)

*Primary Examiner* — Scott J Sugarman
*Assistant Examiner* — Sharrief Broome
(74) *Attorney, Agent, or Firm* — Carter, DeLuca, Farrell & Schmidt, LLP (57) ABSTRACT

Provided is an ophthalmologic apparatus capable of executing accurate automatic alignment even for an eye having an intraocular lens (IOL) implanted therein. The ophthalmologic apparatus includes: an optical system including a light beam projecting unit for projecting a light beam to an eye to be inspected, and a light receiving unit for receiving a reflection light beam from the eye to be inspected; a detecting unit for detecting a plurality of bright spot images from the reflection light beam received by the light receiving unit; and a calculating unit for calculating an alignment status between the eye to be inspected and the optical system based on the detected plurality of bright spot images. The ophthalmologic apparatus is further provided with a selection unit for selecting bright spot images to be used for the calculation by the calculating unit, from among the plurality of bright spot images.

7 Claims, 8 Drawing Sheets

(58) Field of Classification Search
CPC ....... A61B 3/107; A61B 3/0091; A61B 3/145; A61B 3/112; A61B 3/024; A61B 3/103; A61B 3/1241; A61B 3/152; A61B 5/4863; A61B 3/032; A61B 3/036; A61B 3/1208
USPC ....... 351/208, 245, 200, 205, 206, 210, 212, 351/244, 246
See application file for complete search history.

(56) References Cited

U.S. PATENT DOCUMENTS

| | | | | |
|---|---|---|---|---|
| 6,135,596 | A | * 10/2000 | Yoshida | A61B 3/152 351/200 |
| 6,164,778 | A | 12/2000 | Takagi et al. | |
| 2003/0053072 | A1 | * 3/2003 | Fercher | A61B 3/107 356/497 |
| 2004/0008322 | A1 | 1/2004 | Ogawa | |
| 2006/0146285 | A1 | 7/2006 | Hirohara et al. | |
| 2008/0284981 | A1 | * 11/2008 | Fercher | A61B 3/102 351/221 |
| 2010/0142780 | A1 | * 6/2010 | Yasuno et al. | 382/131 |
| 2011/0032481 | A1 | * 2/2011 | Uchida et al. | 351/208 |

FOREIGN PATENT DOCUMENTS

| | | |
|---|---|---|
| JP | H024311 A | 1/1990 |
| JP | 02-119837 A | 5/1990 |
| JP | H11-206710 A | 8/1999 |
| JP | 2003 290146 | * 10/2003 |
| JP | 2003290146 | * 10/2003 |
| JP | 3576656 B | 10/2004 |
| JP | 2005-046245 A | 2/2005 |
| JP | 2007-089715 A | 4/2007 |
| JP | 2011-136109 A | 7/2011 |
| JP | 4769365 B | 9/2011 |
| JP | 2012-504010 A | 2/2012 |
| KR | 101647287 B1 | 8/2016 |

OTHER PUBLICATIONS

Korean Office Action issued in corresponding application No. 10-2013-0085839 on Aug. 20, 2015.
Korean Office Action issued in corresponding application No. 10-2013-0085840 on Aug. 20, 2015.
Chinese Office Action issued in corresponding application No. 201310325640.5 on Aug. 13, 2015.
Office Action issued in corresponding Japanese Application No. 2012-167921 on May 10, 2016.
Office Action issued in corresponding Japanese Application No. 2012-167919 on May 12, 2016.
Office Action issued in corresponding Japanese Patent Application No. 2012-167921 on Nov. 8, 2016.
Japanse Office Action issued in corresponding application 2012-167920 on May 31, 2016.
Office Action issued in corresponding Malaysian Application No. PI2013002789 on Jan. 13, 2017.

* cited by examiner

OPHTHALMOLOGIC APPARATUS AND ALIGNMENT METHOD

BACKGROUND OF THE INVENTION

Field of the Invention

The present invention relates to an ophthalmologic apparatus for measuring ocular characteristics of an eye to be inspected or acquiring an image of the eye to be inspected, and to an alignment method for the ophthalmologic apparatus.

Description of the Related Art

In conventional ophthalmologic apparatus for measuring ocular characteristics of an eye to be inspected, automatic alignment has been known to be performed by projecting a light beam to a cornea of the eye to be inspected and detecting a reflection image of the light beam by a light receiving element to determine an alignment status between the eye and an optical system of the apparatus.

In the ophthalmologic apparatus disclosed in Japanese Patent No. 3576656, a method is disclosed in which the three-dimensional position information on the eye and the optical system of the apparatus is detected from a positional relationship of the reflection image that is received after being separated by a pair of light deflecting members.

In the ophthalmologic apparatus disclosed in Japanese Patent No. 4769365, in order to allow high-precision automatic alignment in a wide range, there has been known a method in which the cornea of the eye to be inspected is irradiated with light beams from an optical axis direction and a direction different from an optical axis to perform the automatic alignment based on reflection images of the light beams.

A cataract patient has surgery to implant an intraocular lens (IOL) in place of a crystalline lens.

However, the IOL has a refractive index higher than that of the crystalline lens, and the light beam projected to the cornea is reflected as IOL reflection light. Therefore, there has been a problem in which an IOL reflection ghost is incorrectly detected as an original alignment reflection image and the automatic alignment is not completed normally.

Therefore, when the automatic alignment has failed, an inspector manually aligns the apparatus for measurement, and hence the measurement takes time.

SUMMARY OF THE INVENTION

The present invention is to provide an ophthalmologic apparatus and an alignment method for an ophthalmologic apparatus that are capable of resolving the above-mentioned problem and reducing, even for an eye to be inspected having an IOL implanted therein, a load on a subject by accurately performing automatic alignment and reducing measurement time.

In order to solve the above-mentioned problem, an ophthalmologic apparatus according to one embodiment of the present invention includes: an optical system including a light beam projecting unit for projecting a light beam to an eye to be inspected, and a light receiving unit for receiving a reflection light beam obtained by reflection of the light beam on the eye to be inspected; a detecting unit for detecting a plurality of bright spot images from the reflection light beam received by the light receiving unit; a selection unit for selecting bright spot images, which are a part of the detected plurality of bright spot images; and a calculating unit for calculating an alignment status between the eye to be inspected and the optical system based on the bright spot images selected by the selection unit.

According to the present invention, even for the eye to be inspected having the IOL implanted therein, the automatic alignment can be performed accurately. Further, measurement time can be reduced so that loads on the inspector and the subject can be reduced.

Further features of the present invention will become apparent from the following description of exemplary embodiments with reference to the attached drawings.

BRIEF DESCRIPTION OF THE DRAWINGS

FIGS. 5A, 5B and 5C are explanatory diagrams of anterior ocular segment images at the time of automatic alignment by bright spots on a cornea, of which

FIGS. 10A, 10B and 10C are explanatory diagrams of anterior ocular segment images at the time of automatic alignment by extraocular illumination, of which

DESCRIPTION OF THE EMBODIMENTS

The present invention is hereinafter described in detail based on illustrated embodiments.

Figure 1:
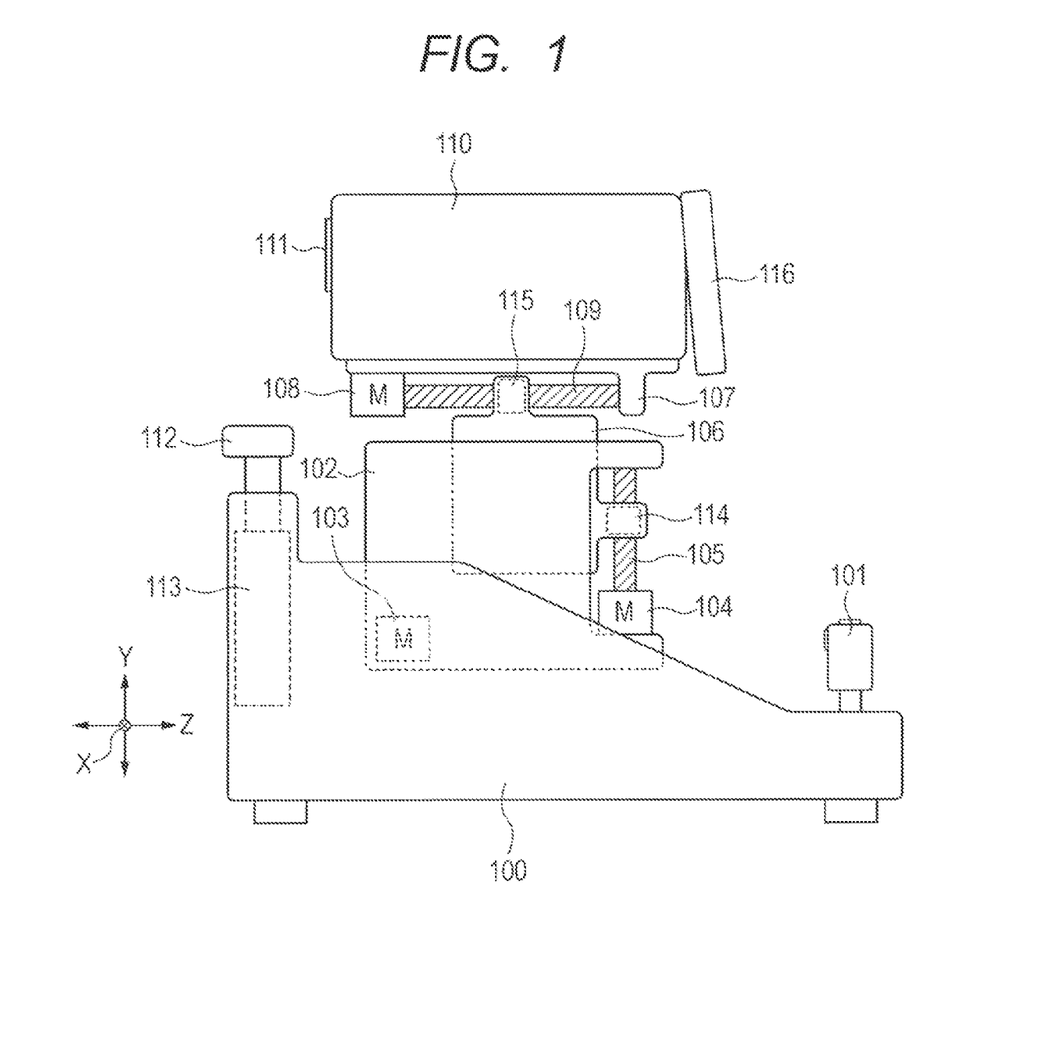
FIG. 1 is an appearance diagram of an ophthalmologic reflectometer according to an embodiment of the present invention.

FIG. 1 is a schematic configuration diagram of an ophthalmologic reflectometer for measuring eye refractive power information as an ophthalmologic apparatus according to an embodiment of the present invention.

A frame 102 is movable in a left-right direction (a direction perpendicular to the drawing sheet, which is hereinafter referred to as X-axis direction) with respect to a base 100. A drive system in the X-axis direction includes an X-axis drive motor 103 fixed on the base 100, a feed screw (not shown) coupled to a motor output shaft, and a nut (not shown), which is movable on the feed screw in the X-axis direction and is fixed to the frame 102. The motor 103 is rotated to move the frame 102 in the X-axis direction via the feed screw and the nut.

A frame 106 is movable in an up-down direction (an up-down direction on the drawing sheet, which is hereinafter referred to as Y-axis direction) with respect to the frame 102. A drive system in the Y-axis direction includes a Y-axis drive motor 104 fixed on the frame 102, a feed screw 105 coupled to a motor output shaft, and a nut 114, which is movable on the feed screw in the Y-axis direction and is fixed to the frame 106. The motor 104 is rotated to move the frame 106 in the Y-axis direction via the feed screw and the nut.

A frame 107 is movable in a front-back direction (a left-right direction on the drawing sheet, which is hereinafter referred to as Z-axis direction) with respect to the frame 106. A drive system in the Z-axis direction includes a Z-axis drive motor 108 fixed on the frame 107, a feed screw 109 coupled to a motor output shaft, and a nut 115, which is movable on the feed screw in the Z-axis direction and is fixed to the frame 106.

The motor 108 is rotated to move the frame 107 in the Z-axis direction via the feed screw 109 and the nut. On the frame 107, a measurement unit 110 for performing measurement (functioning as an acquiring unit for acquiring an eye refractive power, which is one kind of specific information of an eye to be inspected) is fixed.

On an end portion of the measurement unit 110 on a subject side, a light source (not shown) for performing alignment and a light source unit 111 for measuring a cornea curvature are provided.

In addition, on the base 100, a joystick 101, which is an operation member for aligning the measurement unit 110 with respect to an eye to be inspected E, is provided, and at the time of the measurement, the joystick is tilted to perform adjustment of the position and the like.

When an eye refractive power is to be measured, a subject places his/her chin on a chin rest 112 and pushes his/her forehead to a forehead rest portion of a face rest frame (not shown) fixed to the base 100, and hence a position of an eye to be inspected can be fixed.

In addition, the chin rest 112 is adjustable in the Y-axis direction by a chin rest drive system 113 depending on the size of the face of the subject.

On an end portion of the measurement unit 110 on an inspector side, there is provided an LCD monitor 116 as a display member for observing the eye to be inspected E, which can display a measurement result and the like.

(Eye Refractive Power Measurement Unit)

Figure 2:
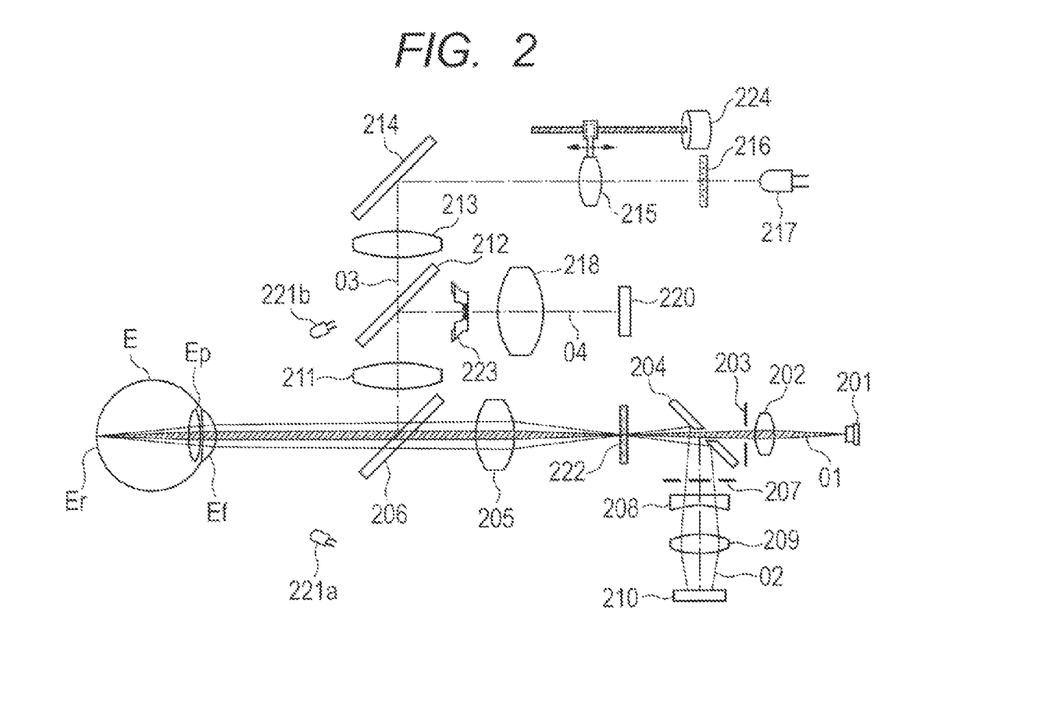
FIG. 2 is an arrangement diagram of an optical system of a measurement portion according to the embodiment illustrated in FIG. 1.

FIG. 2 is an arrangement diagram mainly illustrating an optical system arranged inside the measurement unit 110.

On an optical path 01 from an eye refractive power measurement light source 201 for projecting light having a wavelength of 880 nm to a predetermined part of the eye to be inspected to the eye to be inspected E, a lens 202 and a stop 203 that is substantially conjugate with a pupil Ep of the eye to be inspected E are arranged in the stated order. On the optical path 01, a perforated mirror 204, a lens 205 as a projecting unit, and a dichroic mirror 206 for reflecting all infrared and visible light having wavelengths of less than 880 nm from the eye to be inspected E side and reflecting a part of a light beam having a wavelength of 880 nm or more from the eye to be inspected E side are further arranged in the stated order.

On an optical path 02 in the reflection direction of the perforated mirror 204, there are arranged a stop 207 that is substantially conjugate with the pupil Ep and has a ring-like slit, a light beam dispersion prism 208, a lens 209, and an image pickup element 210 in the stated order.

The above-mentioned optical system is used for measuring the eye refractive power. A light beam emitted from the measurement light source 201 is restricted by the stop 203 and primarily forms an image on the lens 202 before the lens 205. Then, after being transmitted through the lens 205 and the dichroic mirror 206, the light beam is projected to the pupil center of the eye to be inspected E.

The projected light beam is reflected on a fundus, and the fundus reflection light enters the lens 205 again through the pupil center. The entering light beam is transmitted through the lens 205 and then is reflected by a periphery of the perforated mirror 204.

The reflected light beam is separated by pupil separation in the stop 207 substantially conjugate with the pupil Ep of the eye to be inspected E and the light beam dispersion prism 208, and is projected as a ring image to a light receiving plane of the image pickup element 210.

When the eye to be inspected E is an emmetropic eye, this projected ring image becomes a predetermined circle. When the eye to be inspected E is a short-sighted eye, the projected circle becomes smaller than that in the emmetropic eye. When the eye to be inspected E is a long-sighted eye, the projected circle becomes larger than that in the emmetropic eye.

When the eye to be inspected E has astigmatism, the projected ring image becomes an ellipse in which an angle formed between a horizontal axis and the ellipse is an astigmatic axis angle. Based on a coefficient of this ellipse, the eye refractive power is determined.

On the other hand, in the reflection direction of the dichroic mirror 206, there are arranged a fixation target projecting optical system and an alignment light receiving optical system used for both anterior ocular segment observation and alignment detection of the eye to be inspected.

On an optical path 03 of the fixation target projecting optical system, there are arranged a lens 211, a dichroic mirror 212, a lens 213, a reflection mirror 214, a lens 215, a fixation target 216, and a fixation target light source 217 in the stated order.

When the fixation target drive is performed, a projection light beam from the turned-on fixation target light source 217 illuminates the fixation target 216 from the backside, and is projected to the fundus Er of the eye to be inspected E via the lens 215, the reflection mirror 214, the lens 213, the dichroic mirror 212, and the lens 211.

Note that, the lens 215 can be moved in an optical axis direction by a fixation target drive motor 224 so as to perform diopter drive of the eye to be inspected E to realize a fogged state of the eye to be inspected E.

On an optical path 04 in the reflection direction of the dichroic mirror 212, there are arranged an alignment prism stop 223 that is inserted and removed by an alignment prism stop insert/remove solenoid (not shown), a lens 218, and an image pickup element 220 in the stated order.

The alignment prism stop 223 may be inserted and removed to perform the alignment when the alignment prism stop 223 is on the optical path 04 and to perform the observation of the anterior ocular segment or transillumination observation when the alignment prism stop 223 is retracted from the optical path.

Figure 3:
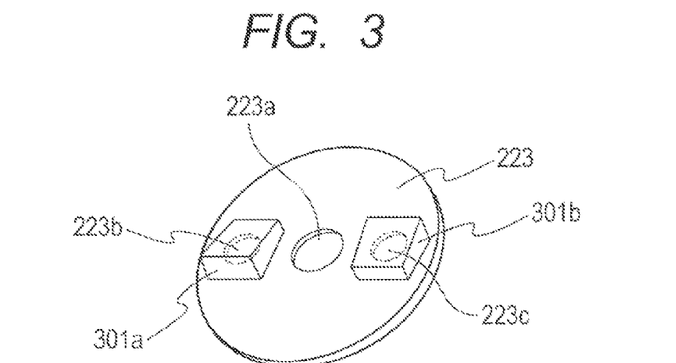
FIG. 3 is a perspective view of an alignment prism stop.

FIG. 3 illustrates a shape of the alignment prism stop 223. Three apertures 223a, 223b, and 223c are formed in a disk-shaped stop plate, and alignment prisms 301a and 301b, each of which transmits only a light beam having a wavelength of about 880 nm, are affixed to the dichroic mirror 212 side of the apertures 223b and 223c at the sides.

Diagonally in front of the anterior ocular segment of the eye to be inspected E, anterior ocular segment illuminating light sources 221a and 221b having wavelengths of about 780 nm are arranged. An anterior ocular segment image of the eye to be inspected E illuminated by the anterior ocular segment illuminating light sources 221a and 221b is formed on a light-receiving sensor surface of the image pickup element 220 via the dichroic mirror 206, the lens 211, the dichroic mirror 212, and the center aperture 223a of the alignment prism stop.

A light source for detecting the alignment is used also as the measurement light source 201 for measuring the eye refractive power described above. At the time of the alignment, a translucent diffuser panel 222 is inserted to the optical path by a diffuser panel insert/remove solenoid (not shown).

A position at which the diffuser panel 222 is inserted is substantially the position at which the measurement light source 201 described above primarily forms the image by the projection lens 202, and is a focal position of the lens 205. In this manner, an image of the measurement light source 201 is once formed on the diffuser panel 222, and the image becomes a secondary light source so that the lens 205 projects a thick collimated light beam toward the eye to be inspected E.

The collimated light beam is reflected by a cornea Ef of the eye to be inspected to form a bright spot image. Then, a part of the light beam is reflected again by the dichroic mirror 206, transmitted through the lens 211, and reflected by the dichroic mirror 212. Further, the light beam is transmitted through the apertures 223b and 223c and the alignment prisms 301a and 301b of the alignment prism stop and converged by the lens 218, and forms images on the image pickup element 220.

The center aperture 223a of the alignment prism stop 223 is configured to transmit the light beams having the wavelengths of 780 nm or more of the anterior ocular segment illuminating light sources 221a and 221b. Therefore, the reflection light beam from the anterior ocular segment illuminated by the anterior ocular segment illuminating light sources 221a and 221b follows the observation optical system as with the path of the reflection light beam from the cornea Ef, and is transmitted through the aperture 223a of the alignment prism stop 223 to form an image by the image forming lens 218 on the image pickup element 220.

Further, the light beam that has been transmitted through the alignment prism 301a is refracted downward, and the light beam that has been transmitted through the alignment prism 301b is refracted upward. The alignment of the eye to be inspected E may be performed based on the positional relationship of the light beams that have transmitted through the stop.

(System Control Portion)

Figure 4:
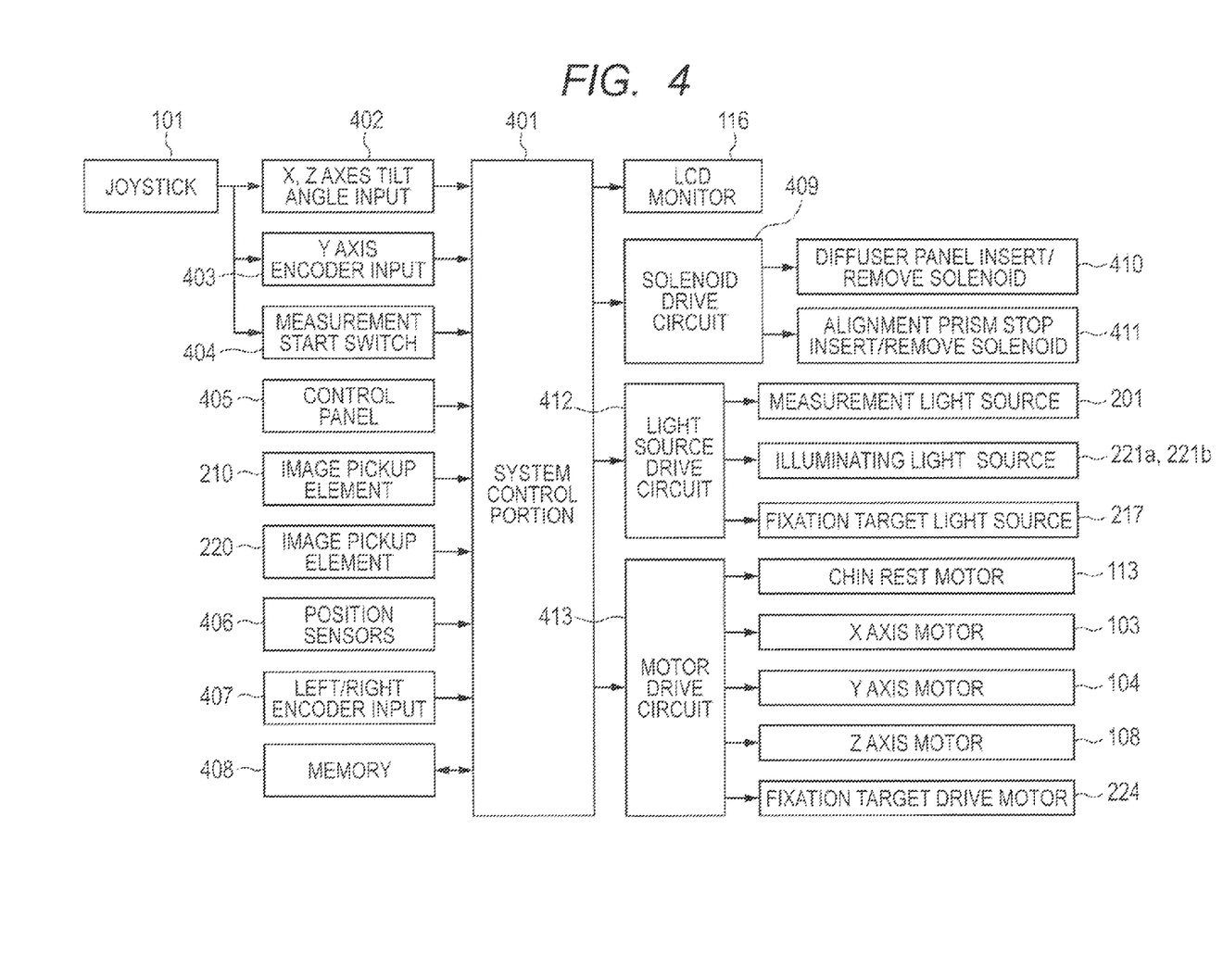
FIG. 4 is a system block diagram of the ophthalmologic reflectometer according to the embodiment of the present invention.

FIG. 4 is a system block diagram. A system control portion 401 that controls the entire system includes a program storage portion, a data storage portion for storing data for correcting an eye refractive power value, an input and output control portion for controlling input and output with various devices, and a calculation processing portion for calculating data obtained from various devices.

To the system control portion 401, the joystick 101 for aligning the measurement unit 110 with respect to the eye to be inspected E and starting the measurement is connected. To the system control portion 401, an X, Z axes tilt angle input 402 for tilts of the joystick 101 to the front, back, left, and right, a Y axis encoder input 403 for rotation of the joystick 101, and a measurement start switch 404 for pressing of a measurement start button are also connected. In addition, on a control panel 405 provided to the base 100 (see FIG. 1), a print switch, a chin rest up/down switch, and the like are arranged, and when a switch input is made, the system control portion is notified of a signal.

The anterior ocular segment image of the eye to be inspected E picked up by the image pickup element 220 is stored in a memory 408. A pupil image and a corneal reflection image of the eye to be inspected E are extracted from the image stored in the memory 408 to detect alignment. Further, the anterior ocular segment image of the eye to be inspected E picked up by the image pickup element 220 is combined with text and graphic data, and the anterior ocular segment image, measured values, and the like are displayed on the LCD monitor 116.

The ring image for calculating the eye refractive power, which is picked up by the image pickup element 210, is stored in the memory 408.

A diffuser panel insert/remove solenoid 410 and an alignment prism stop insert/remove solenoid 411 are driven and controlled by a command from the system control portion 401 via a solenoid drive circuit 409. Further, the X axis motor 103, the Y axis motor 104, the Z axis motor 108, the chin rest motor 113, and the fixation target drive motor 224 are driven by a command from the system control portion 401 via a motor drive circuit 413.

The measurement light source 201, the extraocular illuminating light sources 221a and 221b, and the fixation target light source 217 are controlled to be turned on or off and changed in light amount by a command from the system control portion 401 via a light source drive circuit 412.

(Description of Operation)

Operation of the apparatus including the above-mentioned components is described.

Figure 5A:
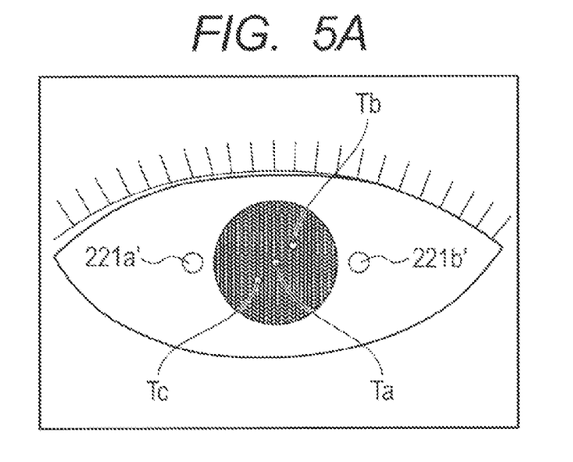
FIG. 5A illustrates an anterior ocular segment image in a status in which the alignment is too far.
Figure 5B:
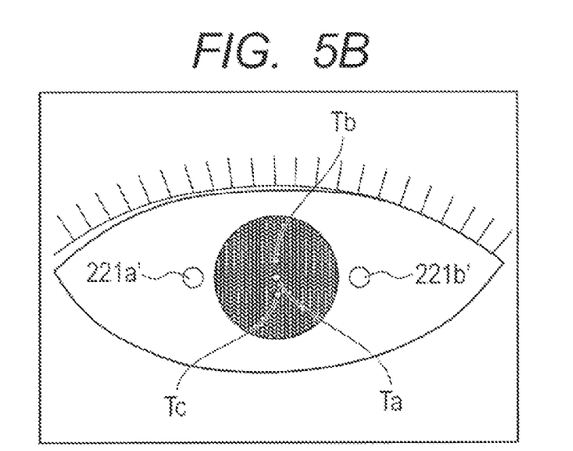
FIG. 5B illustrates an anterior ocular segment image in a status in which the alignment is proper.
Figure 5C:
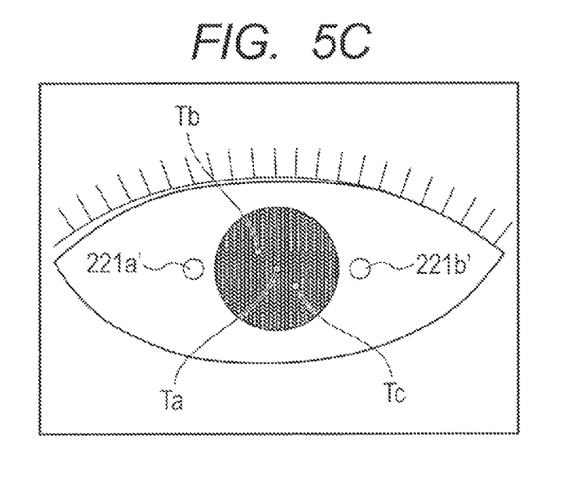
FIG. 5C illustrates an anterior ocular segment image in a status in which alignment is too close.

As illustrated in FIGS. 5A to 5C, at the time of alignment, cornea bright spots, which are obtained by reflection on a cornea Ec, are picked up by the image pickup element 220 as indices Ta, Tb, and Tc. In other words, the light beams divided by the apertures 223a, 223b, and 223c and the prisms 301a and 301b of the alignment prism stop 223 form the indices Ta, Tb, and Tc on the image pickup element 220. In addition, bright spot images 221a' and 221b' formed by the extraocular illuminating light sources 221a and 221b are picked up by the image pickup element 220 along with the anterior ocular segment of the eye to be inspected illuminated by the extraocular illuminating light sources 221a and 221b.

When three bright spots Ta, Tb, and Tc are successfully detected, the system control portion 401 controls the motor drive circuit 413 to drive the measurement unit 110 in the up-down and left-right directions (X- and Y-axis directions) so as to match the center bright spot Ta with a center direction. Next, the system control portion 401 further drives the measurement unit 110 in the front-back direction (Z-axis direction) so that the bright spots Tb and Tc are arrayed in the vertical direction with respect to the bright spot Ta. As illustrated in FIG. 5B, the alignment is completed in a status in which the three bright spots Ta, Tb, and Tc on the cornea are arrayed in the vertical direction.

Improper alignment statuses are as illustrated in FIG. 5A when the alignment is too far, and as illustrated in FIG. 5C when the alignment is too close.

In order to measure the eye refractive power, the system control portion 401 retracts the diffuser panel 222, which has been inserted to the optical path 01 for the automatic alignment, from the optical path 01. The system control portion 401 adjusts the light amount of the measurement light source 201 and projects a measurement light beam to the fundus Er of the eye to be inspected E.

Reflection light from the fundus follows the optical path 02 and is received by the image pickup element 210. The picked-up fundus image is projected in a ring shape by the ring stop 207 due to the refractive power of the eye to be inspected. This ring image is stored in the memory 408.

Barycentric coordinates of the ring image stored in the memory 408 are calculated, and an ellipse equation is determined. A major axis, a minor axis, and a tilt angle of the major axis of the determined ellipse are calculated so that the eye refractive power value in so-called preliminary measurement of the eye to be inspected E is calculated. This preliminary measurement is used to determine whether the eye to be inspected E is myopic or hyperopic.

Based on the calculated eye refractive power value, the fixation target drive motor 224 is driven to a position corresponding to the refractive power value via the motor drive circuit 413, and the lens 215 is moved to present the fixation target 216 to the eye to be inspected E at a refractivity corresponding to a refractivity of the eye to be inspected E.

Thereafter, the lens 215 is moved away by a predetermined amount so as to fog the fixation target 216, and the measurement light source is turned on again for the measurement of the eye refractive power. In this manner, the measurement of the eye refractive power, the fogging by the fixation target 216, and the measurement of the eye refractive power are repeated so that a final measured value at which the refractive power is stabilized may be obtained.

First Embodiment

Figure 6:
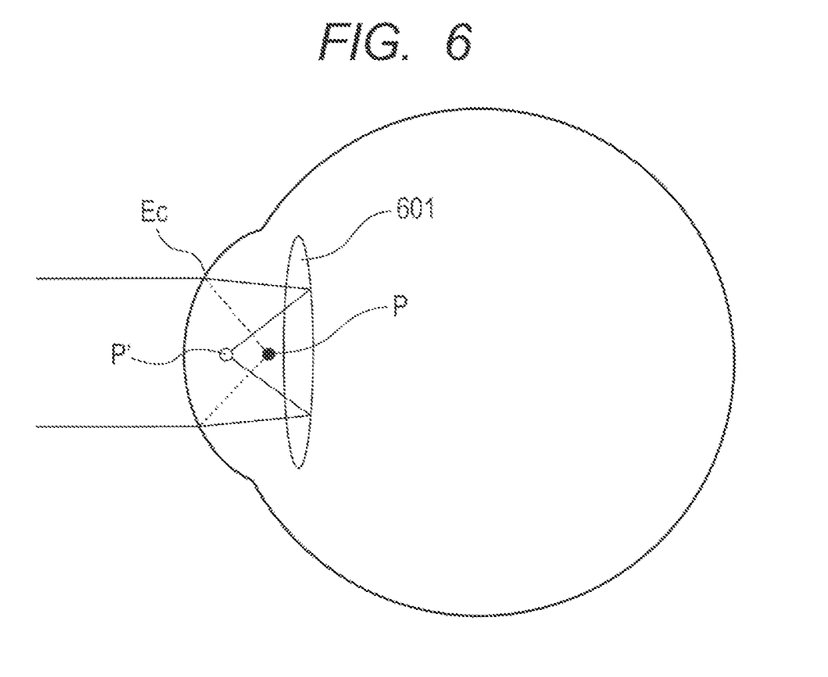
FIG. 6 is a diagram illustrating bright spots on a cornea of an IOL-implanted eye.

FIG. 6 illustrates the bright spots on the cornea in an IOL-implanted eye. A part of the projection light beam is reflected on the cornea Ec so that a virtual image P is formed by corneal reflection. Another part of the projection light beam that is not reflected on the cornea is reflected on an IOL 601 to form a real image P'. The real image P' is formed at a position closer to the cornea than the virtual image P.

Figure 7:
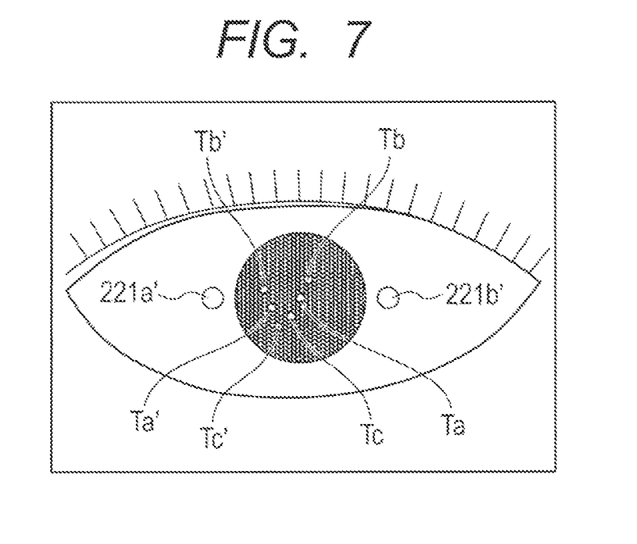
FIG. 7 is a diagram illustrating an anterior ocular segment image of the bright spots on the cornea of the IOL-implanted eye.

FIG. 7 illustrates an image of the anterior ocular segment of the IOL-implanted eye picked up by the image pickup element 220. The bright spots on the cornea are formed as the indices Ta, Tb, and Tc on the image pickup element 220 as described above, and bright spot ghosts on the cornea formed by the reflection on the IOL 601 form indices Ta', Tb', and Tc' on the image pickup element 220.

As illustrated in FIG. 6, IOL reflection ghosts formed by the reflection on the IOL 601 form images at positions closer to the cornea, and hence the indices Ta', Tb', and Tc' are inclined to the left as compared to the indices Ta, Tb, and Tc formed by the bright spots on the cornea. When the automatic alignment is performed from a position at which the alignment status is far based on the indices Ta', Tb', and Tc' formed by the IOL reflection ghosts, the indices Ta', Tb', and Tc' formed by the IOL reflection ghosts are arrayed in the vertical direction prior to the indices Ta, Tb, and Tc formed by the bright spots on the cornea. Therefore, the automatic alignment is completed at the position at which the Z-directional position from the eye to be inspected is far.

By determining whether the indices are formed by the bright spots on the cornea, the indices formed by the IOL reflection ghost are not incorrectly detected, and hence the automatic alignment may be performed accurately.

Figure 8:
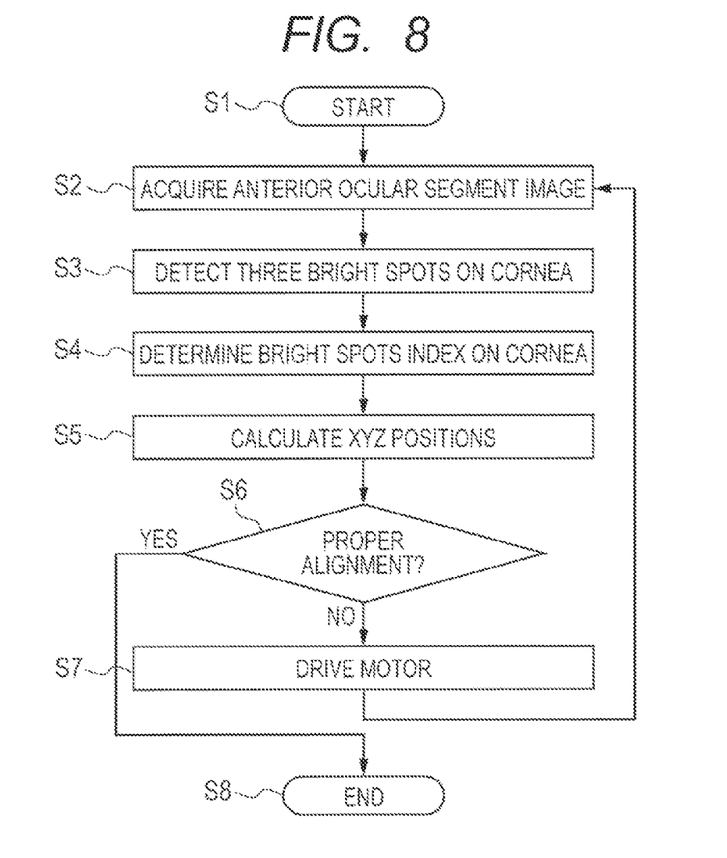
FIG. 8 is a flow chart illustrating an alignment method according to the embodiment of the present invention.

FIG. 8 is a flow chart of the automatic alignment in which the indices formed by the bright spots on the cornea are determined.

In Step S1, an inspector prompts the subject to put his/her chin on the chin rest 112, and makes adjustments with the chin rest drive system 113 so that the position in the Y-axis direction of the eye to be inspected is at a predetermined height. The inspector operates the joystick 101 to a position at which the corneal reflection image of the eye to be inspected E is displayed on the LCD monitor 116 and pushes the measurement start button. When the measurement start button is pushed, the automatic alignment is started.

In the automatic alignment, first, the measurement light source 201 functioning as a light beam projecting unit projects the light beam to the eye to be inspected.

In Step S2, the reflection light beam obtained by the reflection of the light beam on the eye to be inspected is received by the image pickup element 220, and an image of the anterior ocular segment of the eye to be inspected is picked up and stored in the memory 408. The measurement light source 201 and the image pickup element 220 described above, and components associated therewith construct the optical system described above in this embodiment.

Figure 9:
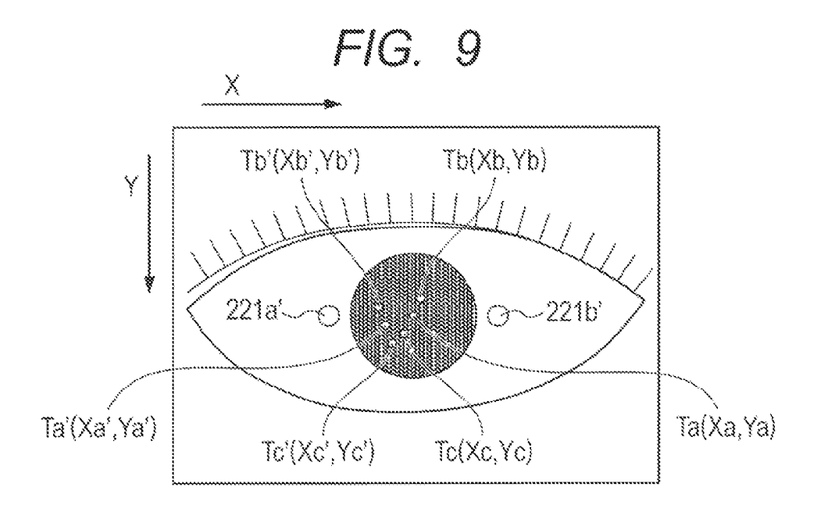
FIG. 9 is a diagram illustrating directions in which the bright spots on the cornea are determined for the IOL-implanted eye.

In Step S3, from the anterior ocular segment image of the eye to be inspected E, which is stored in the memory 408 and illustrated in FIG. 9, three indices formed by the light beams divided by the alignment prism stop 223 are detected. The following two types of indices: the indices Ta, Tb, and Tc formed by the bright spots on the cornea and the indices Ta', Tb', and Tc' formed by the IOL reflection ghosts are detected as candidates of the indices formed by the bright spots on the cornea. The above-mentioned detection of a plurality of bright spot images based on the reflection light beams from the eye to be inspected is executed by a module region functioning as a detecting unit of the system control portion 401 in the present invention.

In the method of detecting the bright spots on the cornea, the indices Ta and Tc divided by the alignment prism stop 223 are at predetermined heights and left-right positions with respect to the index Tb, and hence may be detected through limitation of a detection range. An example of the method of detecting the bright spots on the cornea is described. Firstly, the center bright spot (Ta) of the bright spots on the cornea is detected. Secondly, the upper bright spot (Tb) is detected. The upper bright spot is at a predetermined height position and is located in a predetermined range of the left-right direction with respect to the center bright spot, and hence the detection range may be limited. Thirdly, the lower bright spot (Tc) is detected. The lower bright spot is located in a straight line connecting the upper bright spot and the center bright spot and at a predetermined height with respect to the upper bright spot, and hence the detection range may be limited.

Further, in the first detection, Tb and Tc are also detected as candidates for the center bright spot of the bright spots on the cornea, but because the upper or lower bright spot is not detected in the second and third detections, Tb and Tc are not detected as the center bright spot. Through the above-mentioned detection, all the three bright spots on the cornea may be detected accurately.

In Step S4, determination for selecting which of the indices of the plurality of bright spots on the cornea is used for the alignment is performed. As described above, the indices Ta', Tb', and Tc' formed by the IOL reflection ghosts are inclined to the left as compared to the indices Ta, Tb, and Tc formed by the bright spots on the cornea, and hence the determination is performed as follows. From FIG. 9, the difference of X coordinates of the indices Tb and Tc formed by the bright spots on the cornea is (Xb−Xc), and the difference of X coordinates of the indices Tb' and Tc' formed by the IOL reflection ghost is (Xb'−Xc'). The differences of the X coordinates of the upper and lower indices satisfy (Xb−Xc)>(Xb'−Xc'), and hence the indices having the larger difference of the X coordinates of the upper and lower indices may be determined to be the indices formed by the bright spots on the cornea.

In other words, in a module region functioning as a determining unit of the system control portion 401, of the detected bright spot images arrayed in different straight lines on the cornea, bright spot images arrayed in a straight line having the larger slope are determined to be the bright spot images that are based on the reflection light beams obtained by the reflection on the cornea. Further, in the system control portion 401, a module region functioning as a selection unit in the present invention selects, as bright spot images used for calculating the alignment status, the bright spot images determined to be the bright spot images that are based on the reflection light beams obtained by the reflection on the cornea. Note that, the magnitude of the slope described here is the magnitude of the slope in an XY coordinate system, and when the slope is negative and small in absolute value, the slope is represented as being small. In other words, in a case where a positive value is obtained when a difference of the slopes of the sets of bright spot images constituting the two kinds of straight lines is determined, the straight line of the former term is defined as the straight line having the larger slope.

In Step S5, an XY position is calculated from the position of the selected index Ta (Xa, Ya) of the bright spots on the cornea. A Z position is also calculated from the difference in X coordinates (Xb−Xc) of the indices Tb and Tc of the bright spots on the cornea. With respect to the calculated XYZ positions, a shift amount from an optical axis (center of the image) in the XY direction and a shift amount of (Xb−Xc) from 0 in the Z direction are calculated. The above-mentioned operation is executed by a module region functioning as a calculating unit for calculating the alignment status between the eye to be inspected and the optical system based on the plurality of detected bright spot images in the system control portion 401.

In Step S6, when the XYZ positions calculated in Step S5 are included in an allowable alignment completion range, it is determined that the alignment is complete. When the XYZ positions are not included in the allowable alignment completion range, the processing proceeds to Step S7.

In Step S7, the motor is driven in the XYZ directions by the shift amounts in the XYZ directions calculated in Step S5. After the motor is driven, the processing returns to Step S2, and the motor is continuously driven until it is determined that the alignment is complete.

As described above, the indices formed by the bright spots on the cornea may be determined accurately even for the IOL-implanted eye, and hence incorrect detection of the indices formed by the IOL reflection ghosts is avoided so that the automatic alignment is completed normally.

Note that, in this embodiment, the light beam from the measurement light source 201 as the light beam projecting unit is projected to the eye to be inspected from the direction of the optical path or the optical axis of the reflection light beam. Further, a light receiving unit may be configured to include not only the image pickup element 220 but also the alignment prism stop 223 as a deflection member for deflecting the reflection light beam from the cornea separately to up and down directions.

Second Embodiment

Figure 10A:
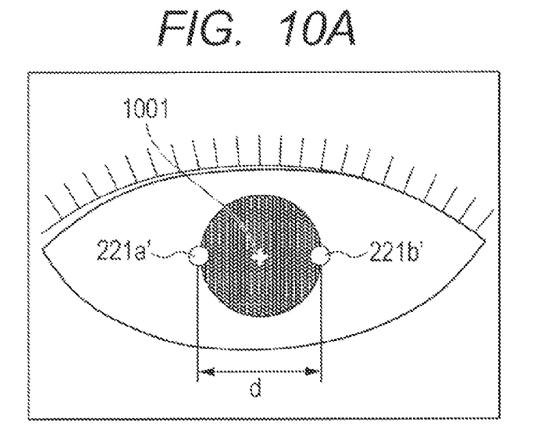
FIG. 10A illustrates an anterior ocular segment image in a status in which alignment is too far.
Figure 10B:
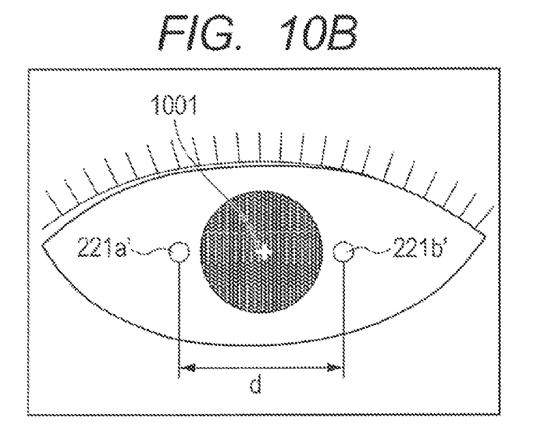
FIG. 10B illustrates an anterior ocular segment image in a status in which the alignment is proper.
Figure 10C:
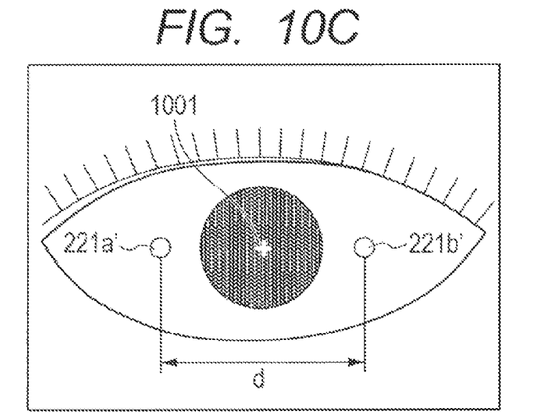
FIG. 10C illustrates an anterior ocular segment image in which the alignment is too close.

FIGS. 10A to 10C are anterior ocular segment images picked up by the image pickup element 220 when corneal reflection bright spot images 221a' and 221b', which are formed by the extraocular illuminating light sources 221a and 221b, are used for detecting alignment instead of the indices of the bright spots on the cornea, which are formed by the measurement light source 201.

FIG. 10B illustrates a case where the alignment is performed properly in the Z direction, and an interval d between the corneal reflection bright spot images 221a' and 221b' has a predetermined value. FIG. 10A illustrates an anterior ocular segment image when the alignment is improperly too far, and the interval d is smaller than the predetermined value. FIG. 10C illustrates an anterior ocular segment image when the alignment is improperly too close, and the interval d is larger than the predetermined value. Therefore, the alignment status in the Z direction may be determined based on the value of the interval d. The alignment status in the XY direction is also determined based on a position of a pupil center 1001.

The interval d also changes depending on a radius of curvature of the eye (subject to individual difference) and hence is not suitable for alignment with high accuracy, but enables detection in a wider range than the alignment by using the bright spots on the cornea. In order to perform the alignment to the extent that the bright spots on the cornea can be detected, the automatic alignment using the corneal reflection bright spot images 221a' and 221b' formed by the extraocular illuminating light sources and the pupil center 1001 is performed.

Specifically, in this embodiment, the function as the light beam projecting unit of the optical system is assumed by the extraocular illuminating light sources 221a and 221b, and the function as the light receiving unit is assumed by the image pickup element 220. The above-mentioned detection of the plurality of bright spot images based on the reflection light beams from the eye to be inspected is executed, as in the case of the first embodiment, by a module region functioning as the detecting unit of the system control portion 401 in the present invention.

Figure 11:
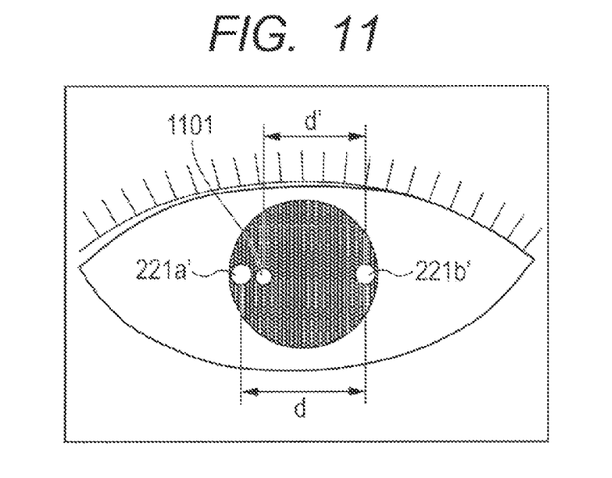
FIG. 11 is a diagram illustrating an anterior ocular segment image with the extraocular illumination for the IOL-implanted eye.

FIG. 11 illustrates an image of the anterior ocular segment of the IOL-implanted eye picked up by the image pickup element 220. The light beams emitted by the extraocular illuminating light sources 221a and 221b form the corneal reflection bright spot images 221a' and 221b' on the image pickup element 220, and due to a part of the light beam that is emitted by the extraocular illuminating light source 221a and is not reflected on the cornea, extraocular illumination reflected on the IOL 601 forms an extraocular illumination IOL reflection ghost 1101 on the image pickup element 220. Note that, in this embodiment, light beams from the extraocular illuminating light sources 221a and 221b as the light beam projecting unit are projected to the eye to be inspected from directions different from the optical path or the optical axis of the reflection light beam.

As described above, the alignment in the Z direction is performed based on the interval d between the corneal reflection bright spot images 221a' and 221b'. When the bright spot image 1101 formed by the extraocular illumination ghost reflected on the IOL 601 is detected, an interval d' is obtained. The interval d' is smaller than the interval d, and hence a position that is too close with respect to the proper alignment position is erroneously determined to be the proper position.

The extraocular illumination is reflected on the cornea Ec, and hence the light amount reaching the IOL 601 is smaller than that of the cornea Ec, with the result that the light amount illuminating the IOL 601 is reduced. With the reduced light amount illuminating the IOL 601, the extraocular illumination ghost reflected on the IOL 601 is smaller in size than extraocular illumination bright spot images reflected on the cornea.

Through the determination on whether the bright spot images are the corneal reflection bright spot images formed by the extraocular illumination, the bright spot image formed by the IOL reflection ghost is not incorrectly detected, and hence the automatic alignment may be performed accurately.

Figure 12:
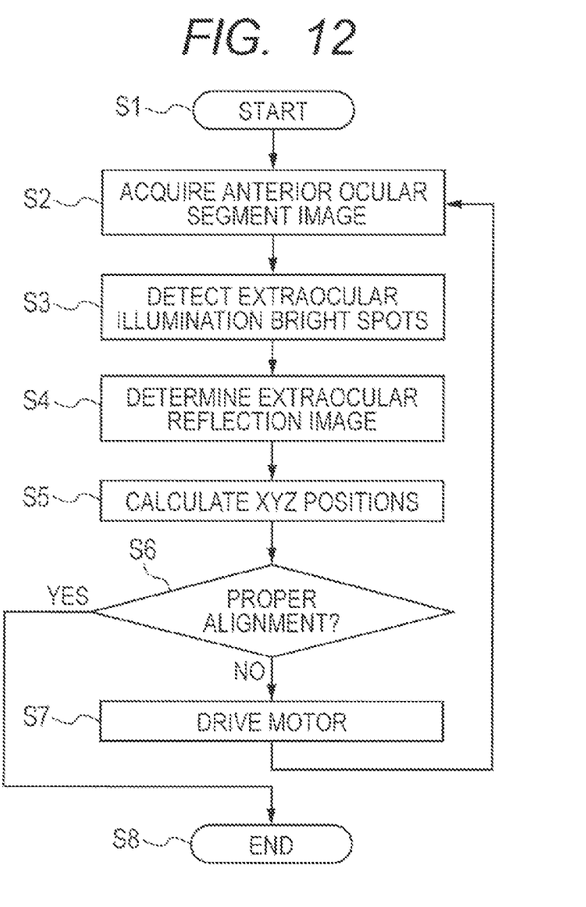
FIG. 12 is a flow chart illustrating an alignment method according to another embodiment of the present invention.

FIG. 12 is a flow chart of the automatic alignment in which the determination of the corneal reflection bright spot image formed by the extraocular illumination is performed.

In Step S1, the inspector prompts the subject to put his/her chin on the chin rest 112, and makes adjustments so that the eye to be inspected is at the predetermined height in the Y-axis direction with the drive system 113. The inspector operates the joystick 101 to a position at which the pupil of the eye to be inspected E is displayed on the LCD monitor 116, and pushes the measurement start button. When the measurement start button is pushed, the automatic alignment is started.

In Step S2, an image of the anterior ocular segment of the eye to be inspected is picked up by the image pickup element 220 and stored in the memory 408.

In Step S3, from the anterior ocular segment image of the eye to be inspected E, which is stored in the memory 408 and illustrated in FIG. 11, the corneal reflection bright spot images 221a' and 221b' formed by the extraocular illuminating light sources 221a and 221b are detected. As candidates of the corneal reflection bright spot images, the corneal reflection bright spot images 221a' and 221b' and the extraocular illumination IOL reflection ghost 1101 are detected. The pupil center is also detected.

In Step S4, the determination of the corneal reflection image is performed. As described above, it is known that the IOL reflection ghost 1101 is smaller in size than the corneal reflection bright spot images 221a' and 221b'. Areas of the candidates of the corneal reflection bright spot images are calculated, and two bright spot images having larger areas may be determined to be the corneal reflection bright spot images.

In other words, in this embodiment, in the module region functioning as the determining unit of the system control portion 401, the bright spot images having larger areas among the plurality of detected bright spot images are determined to be the bright spot images based on the reflection light beam obtained by the reflection on the cornea. In addition, a module region functioning as the selection unit selects those bright spot images as the bright spot images to be used in calculating the alignment status.

In Step S5, an XY position is calculated from the position of the pupil center detected in Step S3. A Z position is also calculated from the interval between two bright spot images that are determined to be the corneal reflection bright spot images in Step S4. With respect to the calculated XYZ positions, a shift amount from an optical axis (center of the image) in the XY direction and a shift amount from a predetermined interval in the Z direction are calculated.

In Step S6, when the XYZ positions calculated in Step S5 are included in an allowable alignment completion range, it is determined that the alignment is complete. When the XYZ positions are not included in the allowable alignment completion range, the processing proceeds to Step S7.

In Step S7, the motor is driven in the XYZ directions by the shift amounts in the XYZ directions calculated in Step S5. After the motor is driven, the processing returns to Step S2, and the motor is continuously driven until it is determined that the alignment is complete.

As described above, the corneal reflection bright spot images formed by the extraocular illumination may be determined accurately even for the IOL-implanted eye, and hence incorrect detection of the IOL reflection ghost image is avoided so that the automatic alignment is completed normally.

Further, in the above description, a case where one IOL reflection ghost occurs is assumed, but similar effects can be obtained also in a case where a plurality of IOL reflection ghosts occur.

In the embodiments, the ophthalmologic reflectometer has been described, but similar effects can be obtained also with a fundus camera, OCT, or the like.

Other Embodiments

Further, the present invention may also be realized by executing the following process. Specifically, software (program) for realizing the functions of the embodiments described above is supplied to a system or an apparatus via a network or an arbitrary type of storage medium, and a computer (CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-167919, filed Jul. 30, 2012, which is hereby incorporated by reference herein in its entirety.

What is claimed is:

1. An ophthalmologic apparatus, comprising:
    an optical system including a light beam projecting unit for projecting a light beam to an eye to be inspected, and a light receiving unit for receiving a reflection light beam obtained by reflection of the light beam on the eye to be inspected;
    a detecting unit for detecting a plurality of bright spot images from the reflection light beam received by the light receiving unit, the bright spot images being generated based on the light beam reflected by an intraocular lens provided in the eye to be inspected and the light beam reflected by a cornea of the eye to be inspected;
    a determining unit for determining whether or not each of the plurality of bright spot images is generated based on the reflection light beam obtained by reflection on a cornea of the eye to be inspected, in accordance with a position of the bright spot images being generated based on the light beam reflected by the intraocular lens and a position of the bright spot images being generated based on the light beam reflected by a cornea of the eye to be inspected in a direction of an optical path of the optical system;
    a selection unit for selecting bright spot images, which are a part of the detected plurality of bright spot images and are determined by the determining unit to be based on the reflection light beam obtained by the reflection on the cornea; and a calculating unit for calculating an alignment status between the eye to be inspected and the optical system based on the bright spot images selected by the selection unit, wherein a bright spot image which is not selected by the selection unit is not used for calculating the alignment status.

2. An ophthalmologic apparatus according to claim 1, wherein the light beam projecting unit projects the light beam to the cornea from a direction of an optical axis of the reflection light beam.

3. An ophthalmologic apparatus according to claim 2, wherein the light receiving unit further includes a deflection member for deflecting the reflection light beam from the cornea separately to up and down directions.

4. An ophthalmologic apparatus according to claim 1, wherein the determining unit determines that a plurality of bright spot image at positions further from the cornea in the direction of the optical path of the optical system are generated based on the reflection light beam obtained by reflection on the cornea of the eye to be inspected, among the bright spot images being generated based on the light beam reflected by the intraocular lens and the light beam reflected by the cornea of the eye to be inspected.

5. An ophthalmologic apparatus, comprising:
an optical system including a light beam projecting unit for projecting a light beam to an eye to be inspected, and a light receiving unit for receiving a reflection light beam obtained by reflection of the light beam on the eye to be inspected;

a detecting unit for detecting a plurality of bright spot images from the reflection light beam received by the light receiving unit, the bright spot images being generated based on the light beam reflected by an intraocular lens provided in the eye to be inspected and the light beam reflected by a cornea of the eye to be inspected;

a determining unit determining, from among bright spot images arrayed in different straight lines of the detected bright spot images on the cornea, the bright spot images arrayed in a straight line having a larger slope to be the bright spot images that are generated based on the reflection light beam obtained by the reflection on the cornea;

a selection unit for selecting bright spot images, which are a part of the detected plurality of bright spot images and are determined by the determining unit to be based on the reflection light beam obtained by the reflection on the cornea of the eye to be inspected; and a calculating unit for calculating an alignment status between the eye to be inspected and the optical system based on the bright spot images selected by the selection unit, wherein a bright spot image which is not selected by the selection unit is not used for calculating the alignment status.

6. An alignment method for an ophthalmologic apparatus, comprising:
projecting, by a light beam projecting unit of an optical system, a light beam to an eye to be inspected;

receiving, by a light receiving unit of the optical system, a reflection light beam obtained by reflection of the light beam on the eye to be inspected;

detecting a plurality of bright spot images from the reflection light beam, the bright spot images being generated based on the light beam reflected by an intraocular lens provided in the eye to be inspected and the light beam reflected by a cornea of the eye to be inspected;

determining, from among bright spot images arrayed in different straight lines, the bright spot images arrayed in a straight line having a larger slope to be the bright spot images generated based on the reflection light beam obtained by reflection on a cornea of the eye to be inspected;

selecting determined bright spot images, which are a part of the plurality of bright spot images, wherein the selecting the bright spot images includes selecting the bright spot images generated based on the light beam reflected by the cornea of the eye to be inspected; and calculating, based on the selected bright spot images, an alignment status between the eye to be inspected and the optical system, wherein a bright spot image which is not selected is not used for calculating the alignment status.

7. A computer-readable storage medium storing a program for causing a computer to execute the steps of the alignment method for an ophthalmologic method according to claim 6.

* * * * *